(12) United States Patent
Sasaki et al.

(10) Patent No.: US 10,690,499 B2
(45) Date of Patent: Jun. 23, 2020

(54) ANALYSIS SYSTEM, ANALYSIS METHOD, AND STORAGE MEDIUM IN WHICH ANALYSIS PROGRAM IS STORED

(71) Applicant: TOPCON CORPORATION, Itabashi-ku, Tokyo (JP)

(72) Inventors: Daisuke Sasaki, Tokyo (JP); Koji Onishi, Tokyo (JP); Masaki Takanashi, Tokyo (JP); Kiyoyasu Takahashi, Tokyo (JP); Shugo Akiyama, Tokyo (JP)

(73) Assignee: TOPCON CORPORATION, Itabashi-ku, Tokyo (JP)

( * ) Notice: Subject to any disclaimer, the term of this patent is extended or adjusted under 35 U.S.C. 154(b) by 0 days.

(21) Appl. No.: 16/139,646

(22) Filed: Sep. 24, 2018

(65) Prior Publication Data

US 2019/0101390 A1  Apr. 4, 2019

(30) Foreign Application Priority Data

Sep. 29, 2017 (JP) .................. 2017-190103

(51) Int. Cl.
  *G01C 15/10* (2006.01)
  *G06T 15/00* (2011.01)
  *A61B 5/107* (2006.01)

(52) U.S. Cl.
  CPC ............ *G01C 15/10* (2013.01); *G06T 15/005* (2013.01); *A61B 5/107* (2013.01); *G06T 2207/10028* (2013.01)

(58) Field of Classification Search
  CPC ......... G06T 7/0075; G06T 2207/10012; G06T 7/0022; G06T 7/0065; G06T 15/04; G06T 17/10; G06T 17/00; G06T 7/0071; H04N 13/0239; H04N 2013/0081
  USPC .................................................. 382/154, 285
  See application file for complete search history.

(56) References Cited

U.S. PATENT DOCUMENTS

| 7,764,809 | B2 | 7/2010 | Ohtomo et al. | |
|---|---|---|---|---|
| 2005/0195384 | A1 | 9/2005 | Ohtomo et al. | |
| 2007/0279590 | A1* | 12/2007 | Ebisawa ................ | A61B 3/113 351/208 |
| 2014/0247439 | A1* | 9/2014 | Neier ...................... | G01C 3/06 356/4.01 |
| 2014/0267623 | A1* | 9/2014 | Bridges .................. | G06T 7/593 348/46 |

(Continued)

FOREIGN PATENT DOCUMENTS

| EP | 3378695 A1 | 9/2018 |
|---|---|---|
| JP | 2001-304865 A | 10/2001 |

(Continued)

*Primary Examiner* — Congvan Tran
(74) *Attorney, Agent, or Firm* — Chiesa Shahinian & Giantomasi PC

(57) ABSTRACT

An analysis system for analyzing inclination of column members includes a laser scanner, a server, and an information terminal. The server includes a data acquisition unit configured to acquire three-dimensional point cloud data of the column members generated by the laser scanner, a surface detector configured to detect surfaces of the column members based on the three-dimensional point cloud data, and an inclination analyzer configured to analyze inclination of the column members by calculating inclination of the surfaces detected by the surface detector.

9 Claims, 7 Drawing Sheets

(56) References Cited

U.S. PATENT DOCUMENTS

| | | | | |
|---|---|---|---|---|
| 2014/0320603 | A1* | 10/2014 | Pettersson | G01C 15/002 |
| | | | | 348/46 |
| 2015/0185000 | A1* | 7/2015 | Wilson | G06N 3/084 |
| | | | | 356/72 |
| 2016/0245918 | A1* | 8/2016 | Becker | G01B 11/26 |
| 2017/0028986 | A1* | 2/2017 | Kuroda | G01S 7/497 |
| 2017/0094251 | A1* | 3/2017 | Wolke | H04N 13/246 |
| 2017/0108528 | A1* | 4/2017 | Atlas | G01B 11/002 |
| 2017/0169604 | A1* | 6/2017 | Van Der Zwan | G06T 7/62 |
| 2018/0075618 | A1* | 3/2018 | Lai | H04N 13/275 |
| 2018/0103210 | A1* | 4/2018 | Park | H04N 5/23296 |

FOREIGN PATENT DOCUMENTS

| | | |
|---|---|---|
| JP | 2005-249715 A | 9/2005 |
| JP | 2009-046946 A | 3/2009 |
| JP | 2017-099068 A | 6/2017 |

\* cited by examiner

ANALYSIS SYSTEM, ANALYSIS METHOD, AND STORAGE MEDIUM IN WHICH ANALYSIS PROGRAM IS STORED

CROSS-REFERENCE TO RELATED APPLICATION

This application claims priority to Japanese Patent Application No. 2017-190103 filed on Sep. 29, 2017, the entire disclosure of which is incorporated by reference herein.

BACKGROUND

The present disclosure relates to an analysis system, an analysis method, and a storage medium in which an analysis program is stored for analyzing inclination of an object to be measured in plumbing the object at a construction site, the object being a long structural member such as a column.

In a construction site of a structure, after erecting column members such as steel columns in position, workers plumb the column members relative to the horizontal plane. This process is referred to as plumbing.

In plumbing, some methods for measuring verticality (plumb) of column members are known. Examples of the methods include a method using a plumb bob and a method using a measuring instrument such as a transit that can determine the verticality of the column members by measuring them in two directions.

A method using linearity of a laser beam for detecting inclination of the column members is known. Specifically, a laser plummet instrument that emits a laser beam vertically downward to the ground is mounted on the upper end of a column member and a point for receiving the laser beam is set at a certain position on the ground. The point is set at such a position that is hit by the laser beam if the column member is erected vertically. Adjusting the inclination of the column member such that the laser dot coincides with the point can plumb the column member (see Japanese Unexamined Patent Publication No. 2001-304865, for example).

When a plumb bob is used in plumbing, the plumb bob swings in high wind, which requires time before the plumb bob stops. When a measuring instrument such as a transit is used, workers need to measure the column member in at least two directions, which requires many work processes and time.

When the technique described in Japanese Unexamined Patent Publication No. 2001-304865 is used, workers need to set-up and remove the laser plummet instrument and the point.

In addition, these methods for plumbing require workers to measure and adjust the inclination of the column members one by one.

As described above, such plumbing methods require many work processes and workers in checking the inclination of the column members, thereby less efficient. Moreover, plumbing accuracy depends largely on experiences and skills of the workers, which results in instability in plumbing accuracy.

Embodiments of the present disclosure have been made to solve the problems above, and the present disclosure intends to provide an analysis system, an analysis method, and a storage medium in which an analysis program is stored that can achieve stable and efficient plumbing.

SUMMARY

To achieve the intention above, the analysis system according to an embodiment of the present disclosure is designed to analyze inclination of an object to be measured, the analysis system including a data acquisition unit configured to acquire three-dimensional point cloud data of the object, a surface detector configured to detect a surface of the object based on the three-dimensional point cloud data, and an inclination analyzer configured to analyze inclination of the object by calculating inclination of the surface detected by the surface detector.

To achieve the object above, the analysis method according to an embodiment of the present disclosure is designed to analyze inclination of an object to be measured, the analysis method including acquiring three-dimensional point cloud data of the object, detecting a surface of the object based on the three-dimensional point cloud data, and analyzing inclination of the object by calculating inclination of the surface detected at the detecting.

To achieve the object above, the storage medium in which an analysis program is stored according to an embodiment of the present disclosure is a non-transitory storage medium designed to store therein an analysis program for analyzing inclination of an object to be measured, the analysis program causing a computer to execute acquiring three-dimensional point cloud data of the object, detecting a surface of the object based on the three-dimensional point cloud data, and analyzing inclination of the object by calculating inclination of the surface detected at the detecting.

Embodiments of the present disclosure having such configurations above can achieve stable and efficient plumbing.

DETAILED DESCRIPTION

The following describes an embodiment of the present disclosure with reference to the accompanying drawings.

Figure 1:
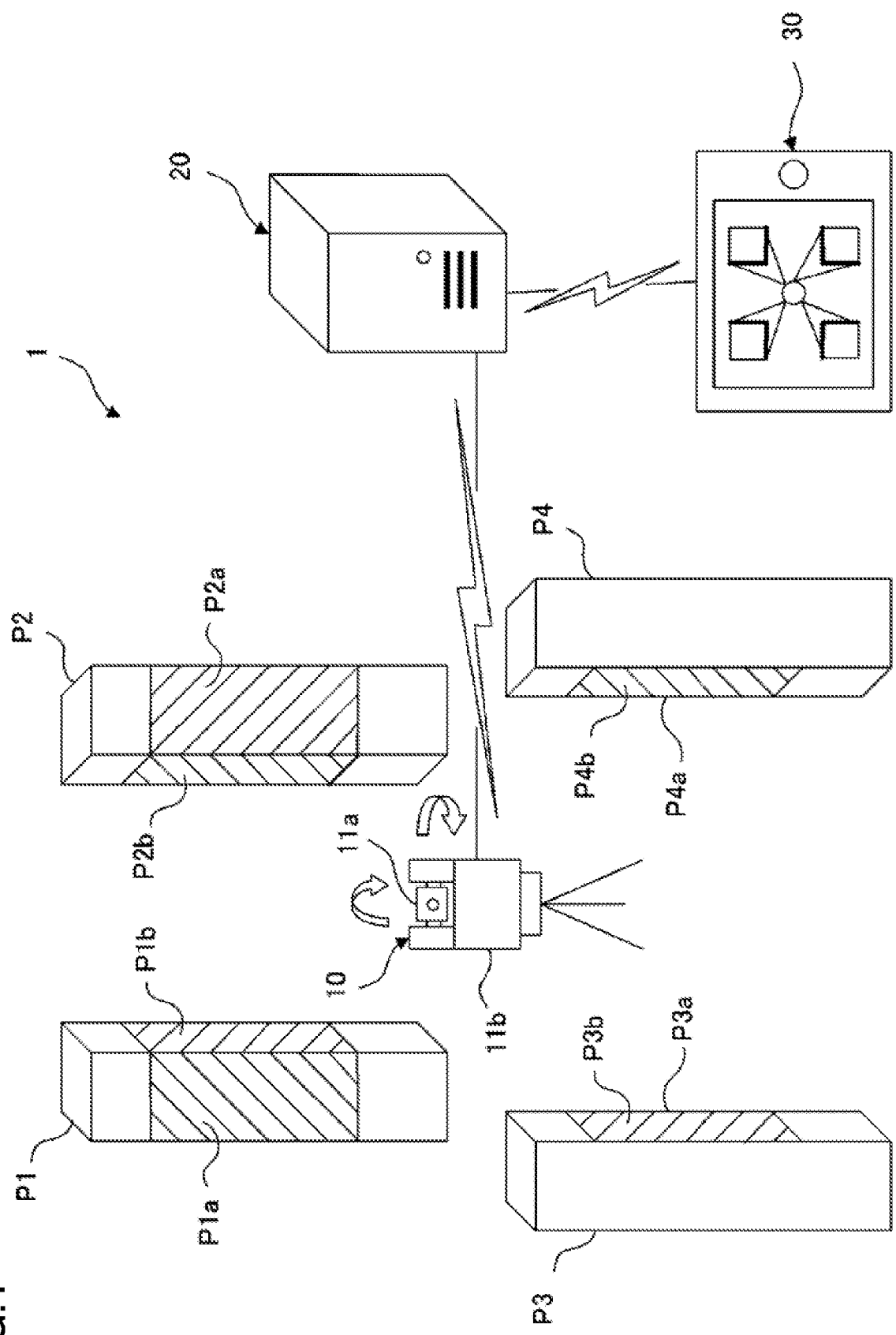
FIG. 1 is a schematic overview of an analysis system according to an embodiment of the present disclosure.
Figure 2:
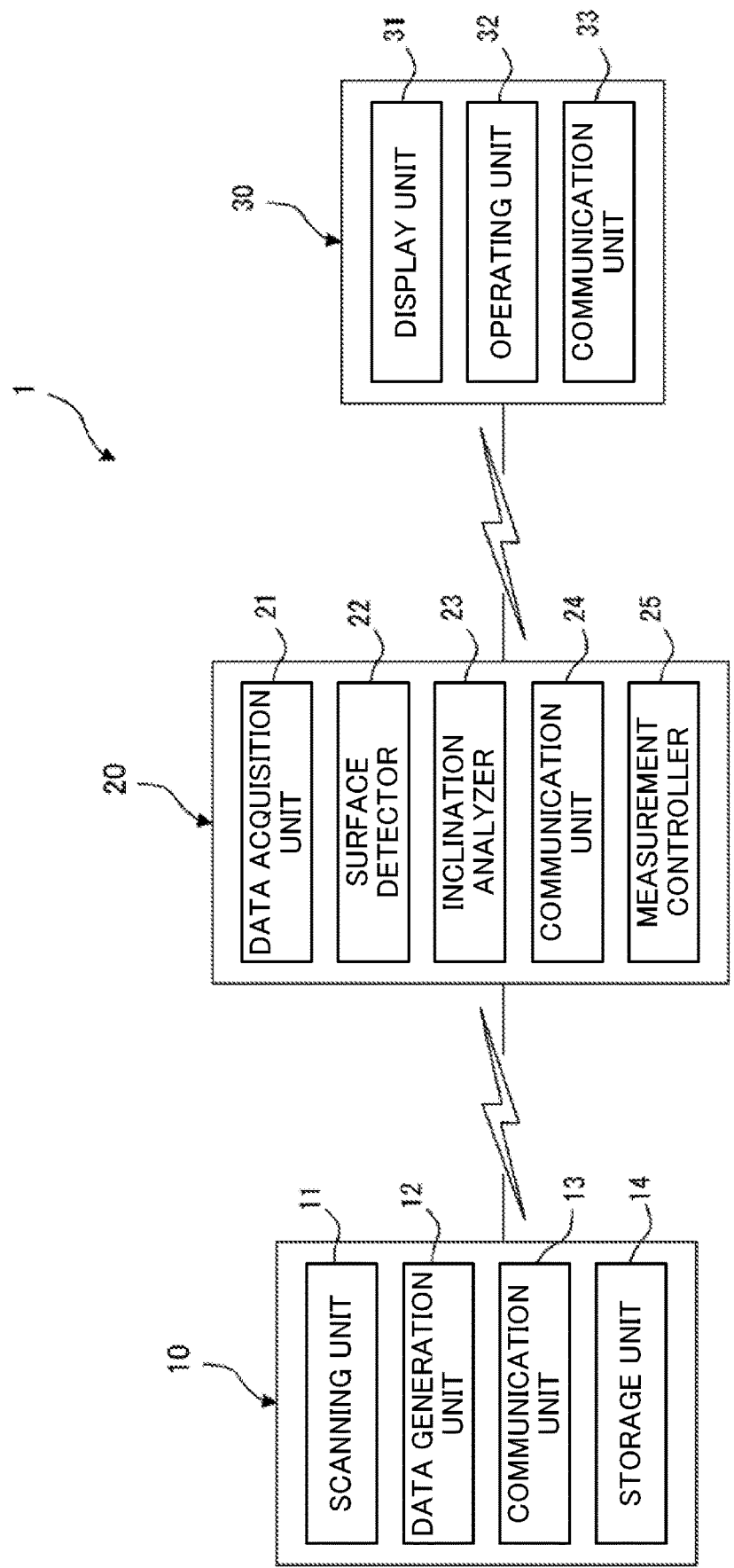
FIG. 2 is a block diagram illustrating a control system of devices included in the analysis system.

Referring to FIGS. 1 and 2, FIG. 1 is a schematic overview of an analysis system according to the embodiment of the present disclosure and FIG. 2 is a block diagram illustrating a control system of devices included in the analysis system that are a laser scanner, a server, and an information terminal. The configuration of the analysis system according to the present embodiment will be described with reference to FIGS. 1 and 2.

In the present embodiment, as illustrated in FIG. 1, an example inclination analysis for four rectangular columns that have been erected in position is described. The four columns, first to fourth column members P1, P2, P3, and P4 are example objects to be measured. The inclination analysis is performed in plumbing the column members. This analysis system 1 includes a laser scanner 10 (measuring device)

that can generate three-dimensional point cloud data by scanning a measurement light beam and receiving the reflected light beam, a server 20 that functions as an analysis device configured to acquire the three-dimensional point cloud data from the laser scanner 10 and analyze the inclination of the column members P1, P2, P3, and P4, and an information terminal 30 that can display the three-dimensional point cloud data including the column members P1, P2, P3, and P4 and a result of the inclination analysis and can set analysis conditions.

The analysis system 1 according to the present embodiment is what is called a cloud computing system that communicably connects the laser scanner 10 with the server 20, and the server 20 with the information terminal 30 via a communication network such as the Internet. In other words, data generated by the laser scanner 10 is transmitted to the server 20 and an analysis result from the server 20 is displayed on the information terminal 30. The information terminal 30 can be used to control the laser scanner 10 via the server 20.

Specifically, as illustrated in FIG. 2, the laser scanner 10 includes a scanning unit 11, a data generation unit 12, a communication unit 13, and a storage unit 14 that are electrically connected with each other. In addition to these units, the laser scanner 10 may include a display unit and an operating unit and may be connected to various types of sensors, which are not illustrated in FIG. 2. The blocks illustrated in FIG. 2 indicate processing functions executed by a computer or parts of the devices in accordance with a computer program. These functions are mainly implemented by an arithmetic processing device such as a central processing unit (CPU).

As illustrated in FIG. 1, the scanning unit 11 includes a distance-measuring unit 11a and a horizontal rotation unit 11b. The distance-measuring unit 11a has a vertically rotatable structure and emits and receives a laser beam (measurement light beam). The horizontal rotation unit 11b supports the distance-measuring unit 11a and has a horizontally rotatable structure. In the scanning unit 11, the horizontal rotation unit 11b rotates the distance-measuring unit 11a in a horizontal direction and the distance-measuring unit 11a swings vertically upward and downward in a certain range and emits and receives a laser beam, or measures a distance. The laser scanner 10 performs scanning operation in this manner. The distance-measuring unit 11a and the horizontal rotation unit 11b are each provided with an angle meter, which is not illustrated. Upon measurement of a distance, the distance and a horizontal angle at which the horizontal rotation unit 11b rotates and a vertical angle at which the distance-measuring unit 11a swings are stored in the storage unit 14. As described above, the scanning unit 11 can scan the measurement light beam horizontally all around the laser scanner 10 and in a certain range in the height direction.

The data generation unit 12 generates three-dimensional point cloud data from the distance, the horizontal angle, and the vertical angle of each focus point acquired in the scanning operation of the scanning unit 11. A three-dimensional model of structures around the laser scanner 10, such as the column members P1, P2, P3, and P4, can be created from the three-dimensional point cloud data. The three-dimensional model can visualize the size and shape of the structures.

The communication unit 13 is a wireless communication unit such as a wireless local area network (LAN). The communication unit 13 is configured to connect to a communication network such as the Internet and transmit and receive information. The communication unit 13 may include a wired communication unit that communicates via a connection terminal (communication units to be described later may also include wired communication units).

The storage unit 14 is, for example, a flash memory or a magnetic disk memory, and is configured to store therein information such as the three-dimensional point cloud data generated by the data generation unit 12.

The server 20 includes a data acquisition unit 21, a surface detector 22, an inclination analyzer 23, a communication unit 24, and a measurement controller 25 that are electrically connected with each other. In addition to these units, the server 20 includes other units such as a storage unit, which are not illustrated, and at least three-dimensional point cloud data and other information can be stored in the storage unit. The storage unit stores therein an analysis program for causing a computer of the server 20 to execute an analysis method, which will be described later.

The data acquisition unit 21 is configured to acquire the three-dimensional point cloud data generated by the laser scanner 10 via the communication unit 24.

The surface detector 22 is configured to detect surfaces of the column members P1, P2, P3, and P4 from the three-dimensional point cloud data acquired by the data acquisition unit 21. Surfaces are detected by, for example, what is called plane fitting. In plane fitting, a plane model is fitted to a three-dimensional model created based on three-dimensional point cloud data. As illustrated in FIG. 1, since the laser scanner 10 in the present embodiment is substantially equally spaced apart from the four column members P1, P2, P3, and P4, the laser scanner 10 detects only two surfaces of each of the column members P1, P2, P3, and P4 close to the laser scanner 10, namely surfaces P1a, P1b, P2a, P2b, P3a, P3b, P4a, and P4b, which may be hereinafter referred to as the surfaces P1a to P4b.

The inclination analyzer 23 is configured to calculate inclination of the surfaces of the column members P1, P2, P3, and P4 detected by the surface detector 22 to calculate inclination of the column members P1, P2, P3, and P4. In the present embodiment, the inclination analyzer 23 calculates inclination of two surfaces of each of the column members P1, P2, P3, and P4 indicated by shaded areas in FIG. 1, and the inclination of the entire column members can be represented by calculating the inclination of the surfaces. The inclination analyzer 23 transmits inclination information of the column members after analysis to a corresponding information terminal 30 via the communication unit 24.

The communication unit 24 is configured to transmit and receive information by connecting to a communication network such as the Internet in the same manner as the communication unit 13 of the laser scanner 10.

The measurement controller 25 is configured to remotely control the laser scanner 10 via the communication unit 24. For example, the measurement controller 25 can control the measurement range of the scanning unit 11 of the laser scanner 10. Specifically, the measurement controller 25 acquires positional information including installation positions of the column members P1, P2, P3, and P4, such as CAD data or other design data, and limits the measurement range of the laser scanner 10 to a certain range including the column members P1, P2, P3, and P4 based on the positional information. Such design data may be acquired (uploaded) from an external device such as the laser scanner 10 or the information terminal 30, or may be stored in the storage unit of the server 20 in advance.

The information terminal 30 includes a display unit 31, an operating unit 32, and a communication unit 33 that are electrically connected with each other. The information terminal 30 may be, for example, a dedicated terminal designed for use with the laser scanner 10, or may be a general-purpose device such as a smartphone or a tablet-type personal computer (PC) installed with an application program for the analysis system. In one preferred embodiment, the information terminal 30 in particular is a portable terminal so that the workers can perform plumbing while checking on the display unit 31.

The display unit 31 is a display configured to acquire inclination information of the column members P1, P2, P3, and P4 calculated by the inclination analyzer 23 of the server 20 and display the information.

The operating unit 32 is configured to receive operations on the information terminal 30 and receive various types of operating instructions and settings to the laser scanner 10. Specifically, the operating unit 32 is configured by, for example, a touch screen integrated with the display unit 31 or configured by one or more buttons.

The communication unit 33 is configured to transmit and receive information by connecting to a communication network such as the Internet in the same manner as the communication unit 13 of the laser scanner 10.

The analysis system 1 having the configuration above is used after the column members P1, P2, P3, and P4 are erected in position. In the analysis system 1, the laser scanner 10 is set, for example, at a position substantially equally spaced apart from the column members P1, P2, P3, and P4 to perform scanning operation and the server 20 acquires three-dimensional point cloud data of the column members P1, P2, P3, and P4, analyzes inclination of column members from inclination of the surfaces of the column members P1, P2, P3, and P4 based on the three-dimensional point cloud data and the information terminal 30 displays the analyzed inclination of the column members.

Figure 3:
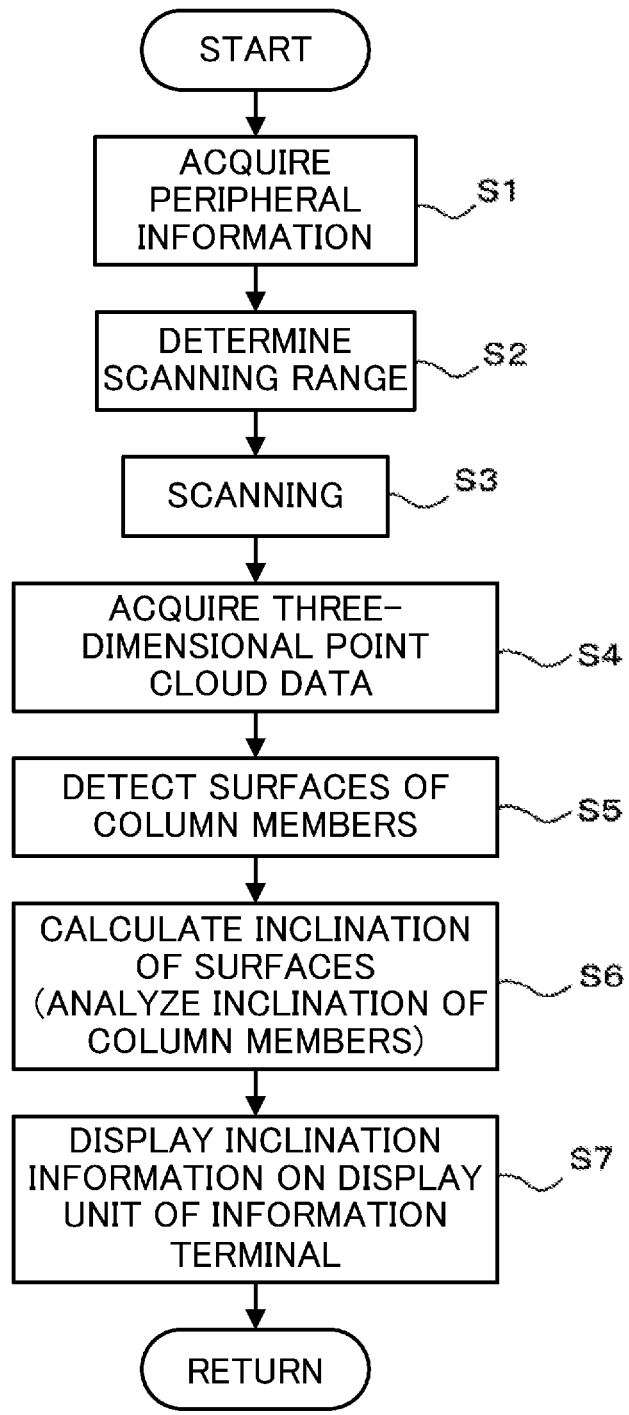
FIG. 3 is a flowchart illustrating a routine for analyzing inclination of column members.
Figure 4A:
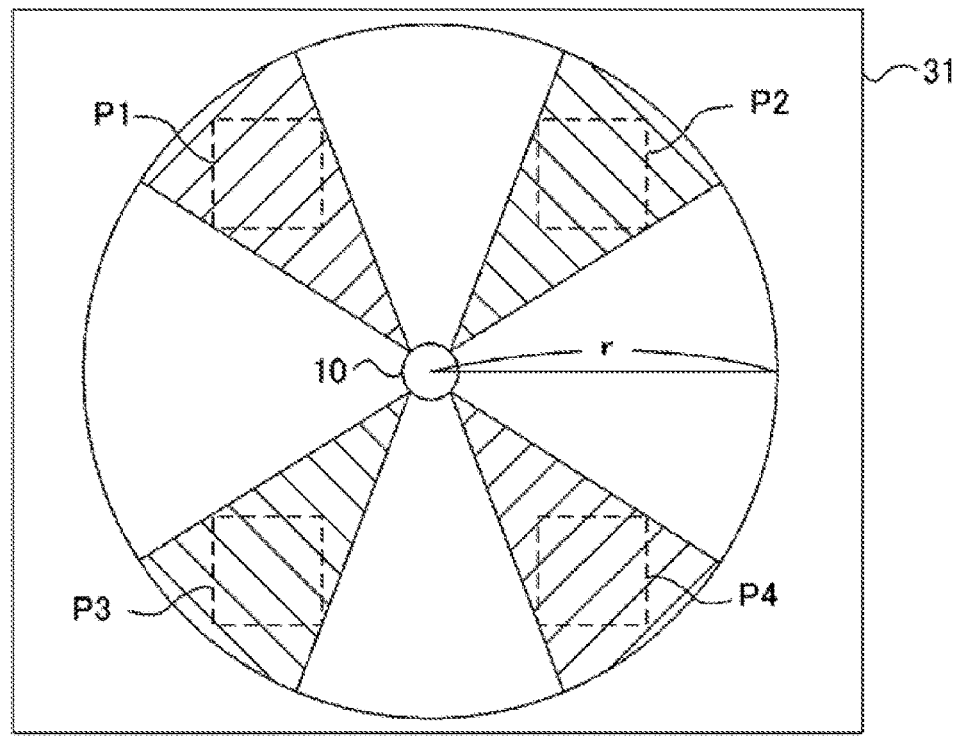
FIG. 4A illustrates a display example of a display unit in setting measurement conditions.
Figure 4B:
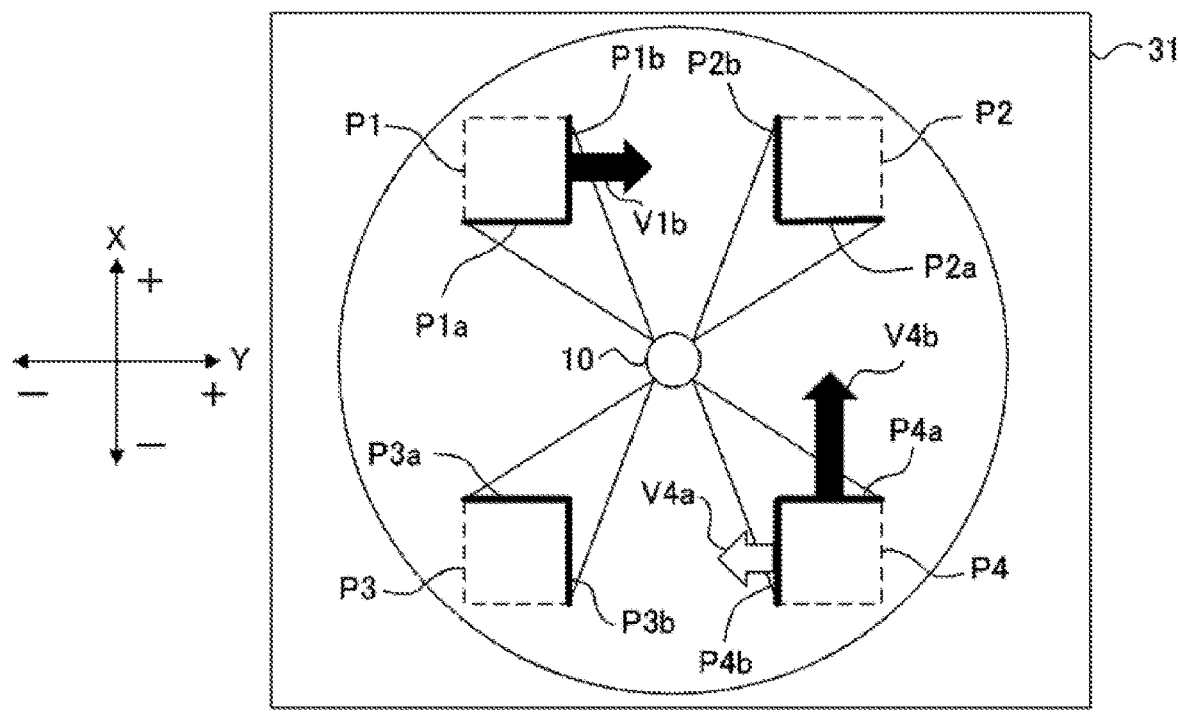
FIG. 4B illustrates a display example of an inclination analysis result.
Figure 5:
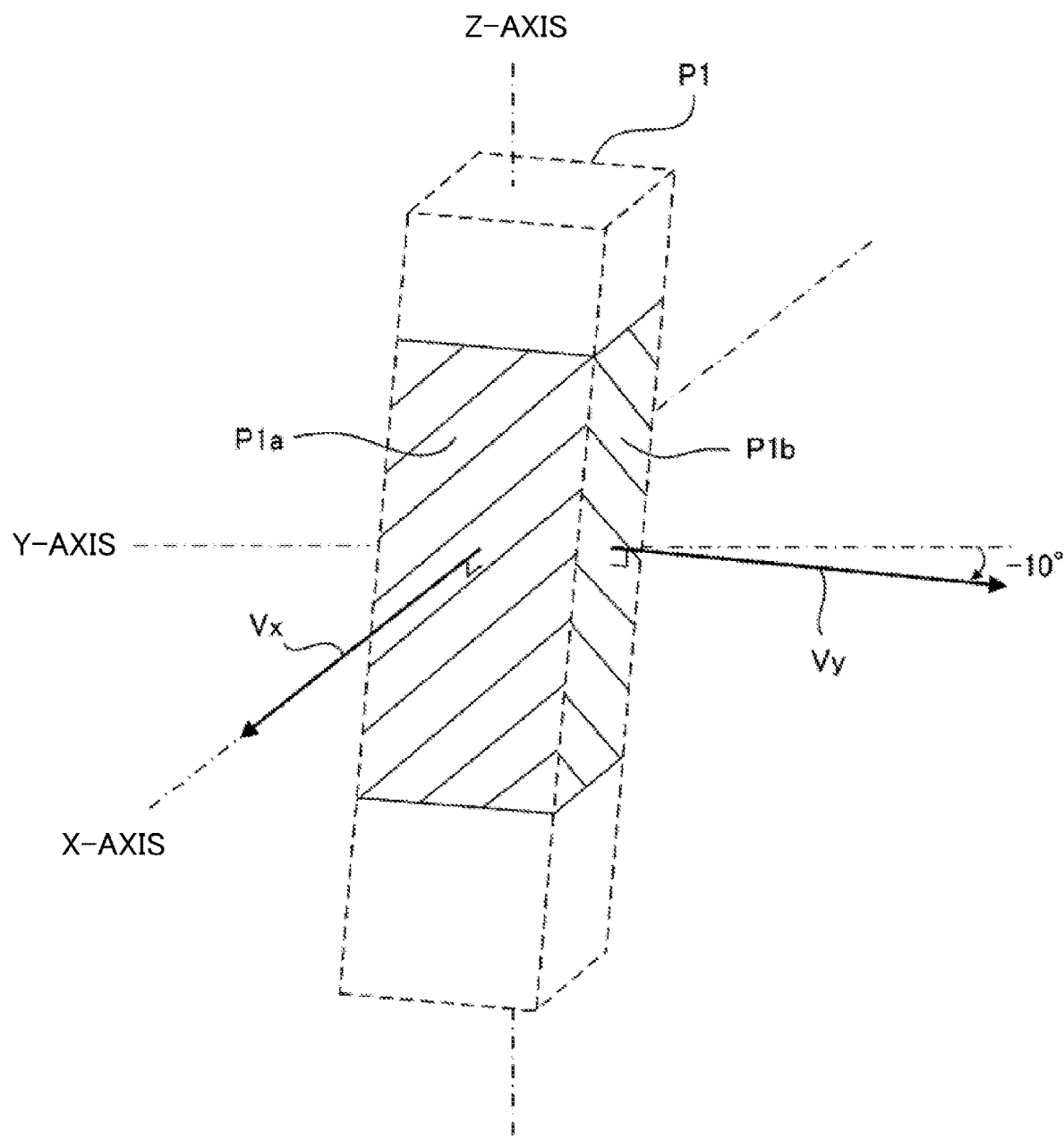
FIG. 5 is a diagram illustrating inclination of a column member.

Specifically, referring to FIGS. 3 to 5, FIG. 3 is a flowchart illustrating a routine for analyzing inclination of the column members in the analysis system according to the present embodiment, FIG. 4A illustrates a display example of the display unit in setting measurement conditions, FIG. 4B illustrates a display example of an inclination analysis result, and FIG. 5 is a diagram illustrating inclination of a column member. The following describes the procedure of the analysis method according to the present embodiment mainly with reference to the flowchart of FIG. 3 and with reference to FIGS. 4A, 4B and 5 as appropriate. Before the analysis routine is started, the laser scanner 10 is set at a position substantially equally spaced apart from the column members P1, P2, P3, and P4 that have been erected in position and the information terminal 30 starts the application program for the analysis system.

At Step S1, the measurement controller 25 of the server 20 reads design data of the construction site including the column members P1, P2, P3, and P4.

At Step S2, the measurement controller 25 of the server 20 sets a measurement range of the laser scanner 10. In setting the measurement range, the display unit 31 of the information terminal 30 in communication with the measurement controller 25 displays a setting screen displaying a measurement range illustrated in, for example, FIG. 4A and the workers can view the setting screen and operate on the screen. Specifically, the display unit 31 displays the position of the laser scanner 10 at substantially the center of the display unit 31 and displays a circle having a measurement radius r with the center coinciding with the position of the laser scanner 10. As indicated by the dashed lines in FIG. 4A, the positions and the shapes of the column members P1, P2, P3, and P4 located within the measurement radius r are displayed in accordance with the design data. A scanning radius and a range of rotation (rotation angle) in the horizontal direction for scanning are automatically or manually set to include the column members P1, P2, P3, and P4, thereby determining measurement ranges as indicated by the shaded areas in FIG. 4A. Although not illustrated, the vertical swinging range of the laser scanner 10 for scanning may be set.

Subsequently, at Step S3, the measurement controller 25 of the server 20 controls the laser scanner 10 to perform scanning operation in the measurement ranges set at Step S2.

At Step S4, after the laser scanner 10 performs at least one cycle of scanning operation around the laser scanner 10, the data acquisition unit 21 of the server 20 acquires three-dimensional point cloud data generated by the data generation unit 12 of the laser scanner 10.

At Step S5, the surface detector 22 of the server 20, as described above, fits a plane model to the shapes of the column members P1, P2, P3, and P4 created based on the three-dimensional point cloud data and detects the surfaces P1a to P4b.

At Step S6, the inclination analyzer 23 of the server 20 calculates inclination of the surfaces P1a to P4b detected at Step S5 and analyzes the inclination of the column members P1, P2, P3, and P4.

For example, FIG. 5 illustrates a state of inclination of the first column member P1. When the surface detector 22 detects, at Step S5, the two surfaces P1a and P1b indicated by the shaded areas as illustrated in FIG. 5, the inclination analyzer 23 defines normal vectors Vx and Vy extending perpendicularly from the surfaces P1a and P1b, respectively. The inclination analyzer 23 calculates angles of the normal vectors in the Z-axis direction relative to the X-Y plane (horizontal plane), and the calculated angles are the inclination angles of the detected surfaces. In FIG. 5, the normal vector Vx extending in the X-axis direction matches the X-axis, which means that the surface P1a is not inclined. The normal vector Vy extending in the Y-axis direction is inclined at 10 degrees downward in the Z-axis direction relative to the Y-axis. In other words, the result of the inclination analysis for the first column member P1 indicates that the first column member P1 is inclined at 10 degrees downward to a side close to the surface P1b.

At Step S7, the inclination analyzer 23 of the server 20 transmits the inclination analysis result calculated at Step S6 to the information terminal 30 and the display unit 31 of the information terminal 30 displays the inclination analysis result.

Specifically, as illustrated in FIG. 4B, the surfaces P1a to P4b detected at Step S5 are indicated by solid lines, whereas the column members P1, P2, P3, and P4 are indicated by dashed lines on the setting screen, and the degree of inclination of the surfaces P1a to P4b are represented by vectors (hereinafter referred to as inclination vectors). The length of the inclination vectors corresponds to the degree of the inclination angle of the surfaces, and a greater inclination angle is represented by a longer vector whereas a smaller angle is represented by a shorter vector. When a surface is inclined downward in the Z-axis direction, the inclination vector is represented by a black arrow, and when inclined upward in the Z-axis direction, the inclination vector is represented by an arrow outline.

In FIG. 4B, the up-down direction corresponds to the X-axis direction and the left-right direction corresponds to the Y-axis direction. The first column member P1 is inclined in the right direction (in the plus direction of the Y-axis) in FIG. 4B. The second and third column members P2 and P3 are not inclined. The fourth column member P4 is inclined in the upward direction (in the plus direction of the X-axis) in FIG. 4B, indicating that the column member P4 is inclined largely downward, and inclined in the left direction (in the minus direction of the Y-axis) in FIG. 4B, indicating that the column member P4 is inclined slightly upward. Workers plumb the column members by adjusting the inclination of the column members in such a direction that reduces the inclination vectors.

After the display unit 31 displays the result of the inclination analysis at Step S7, the routine is returned. Repeating the routine in a short cycle keeps updating the inclination states of the column members P1, P2, P3, and P4, which can in turn keep the workers informed of the current inclination of the column members P1, P2, P3, and P4 in substantially real time, thereby allowing the workers to perform smooth plumbing.

As described above, the analysis system 1 is configured to acquire three-dimensional point cloud data of the column members P1, P2, P3, and P4, detect the surfaces P1a to P4b, and calculate the inclination of the surfaces P1a to P4b to analyze inclination of the column members P1, P2, P3, and P4. Using the three-dimensional point cloud data for analyzing inclination of the column members achieves a collective and highly accurate inclination analysis for the column members P1, P2, P3, and P4 with fewer workers. This system eliminates the need, from plumbing, for checking the inclination of the column members one by one by the workers, and enables a stable and efficient plumbing.

In particular, since the three-dimensional point cloud data is generated by the laser scanner 10 that has a horizontally rotatable and vertically swingable structure, the system can collectively acquire the three-dimensional point cloud data of the column members P1, P2, P3, and P4 in a short time.

Since the measurement controller 25 acquires design data before measurement and limits the measurement range of the laser scanner 10 to a certain range including the column members P1, P2, P3, and P4, the measurement range can be limited to a minimum, thereby allowing the system to acquire the three-dimensional point cloud data in a shorter time.

Since the display unit 31 of the information terminal 30 displays the three-dimensional point cloud data and the inclination of the column members P1, P2, P3, and P4, workers can easily check the inclination of the column members P1, P2, P3, and P4. The workers then plumb the column members in accordance with the information on the display unit 31, which can make plumbing less dependent on the experiences or skills of the workers and achieve a stable and efficient plumbing.

In particular, since the result of the inclination analysis displayed on the display unit 31 is represented by vectors extending from the surfaces of the column members P1, P2, P3, and P4 generated from the three-dimensional point cloud data, this allows the workers to instantly acquire the states of inclination of the column members P1, P2, P3, and P4 and perform plumbing more efficiently.

Although an embodiment of the present disclosure has been described above, the present disclosure is not limited to this.

Although, in the embodiment above, the measurement controller 25 of the server 20 determines the measurement range of the laser scanner 10 in accordance with the design data of the construction site, the information for use in determining the measurement range is not limited to design data.

For example, the measurement controller 25 may acquire information including installation positions of the column members by causing the laser scanner to perform a simplified scan for acquiring the positions of the column members. The simplified scan is a type of scanning that can be finished in a shorter time by reducing the amount of point cloud data acquired in one scanning cycle.

If design data is not prepared in advance, the installation positions of the column members can be acquired by performing the simplified scan to limit the measurement range.

Although, in the embodiment above, inclination of the four column members P1, P2, P3, and P4 is analyzed by using a single laser scanner 10, the relation between the number of laser scanners and the number of column members is not limited to this.

Figure 6:
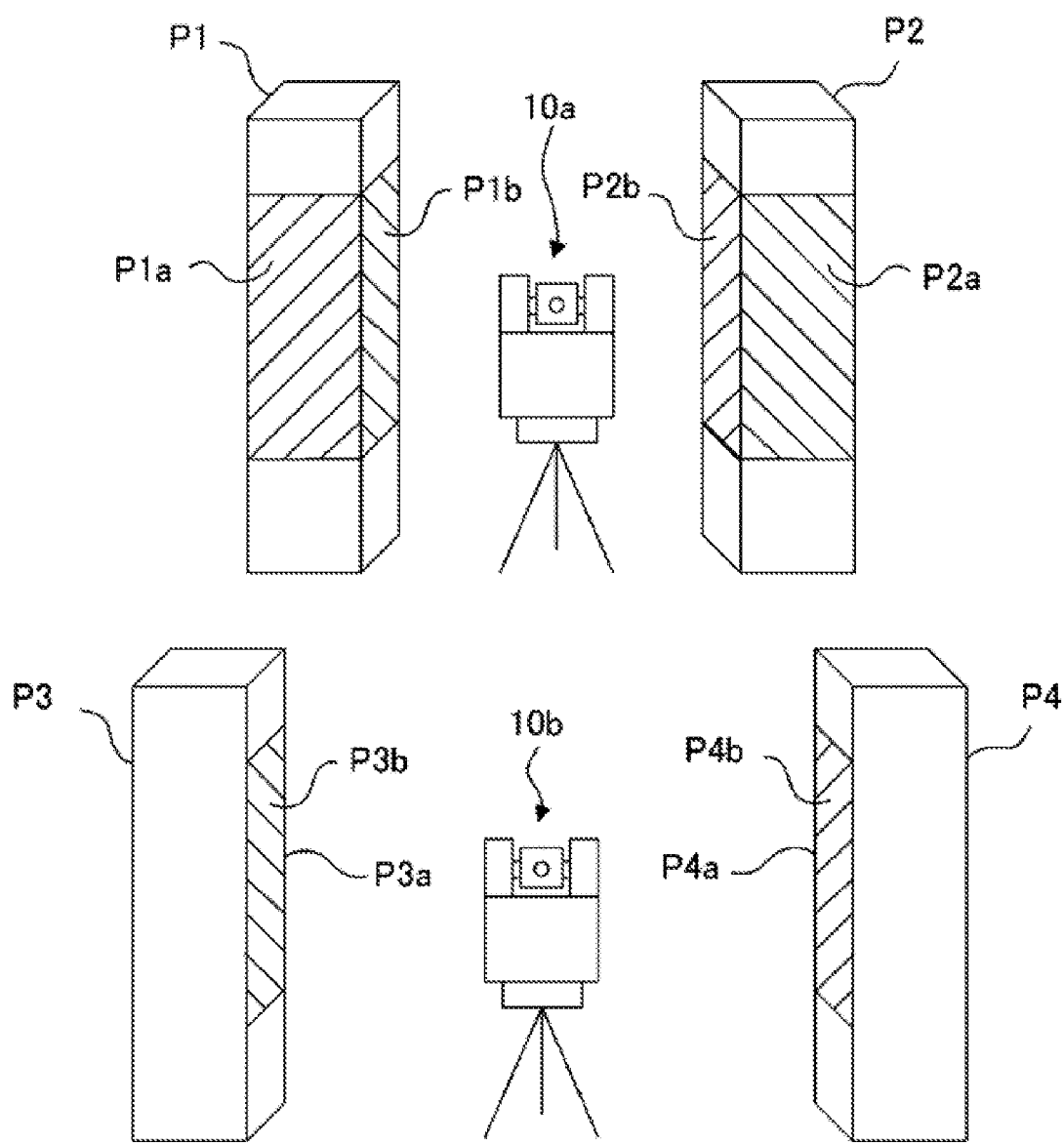
FIG. 6 is a schematic overview of an analysis system according to a modification of the present disclosure.
Figure 7:
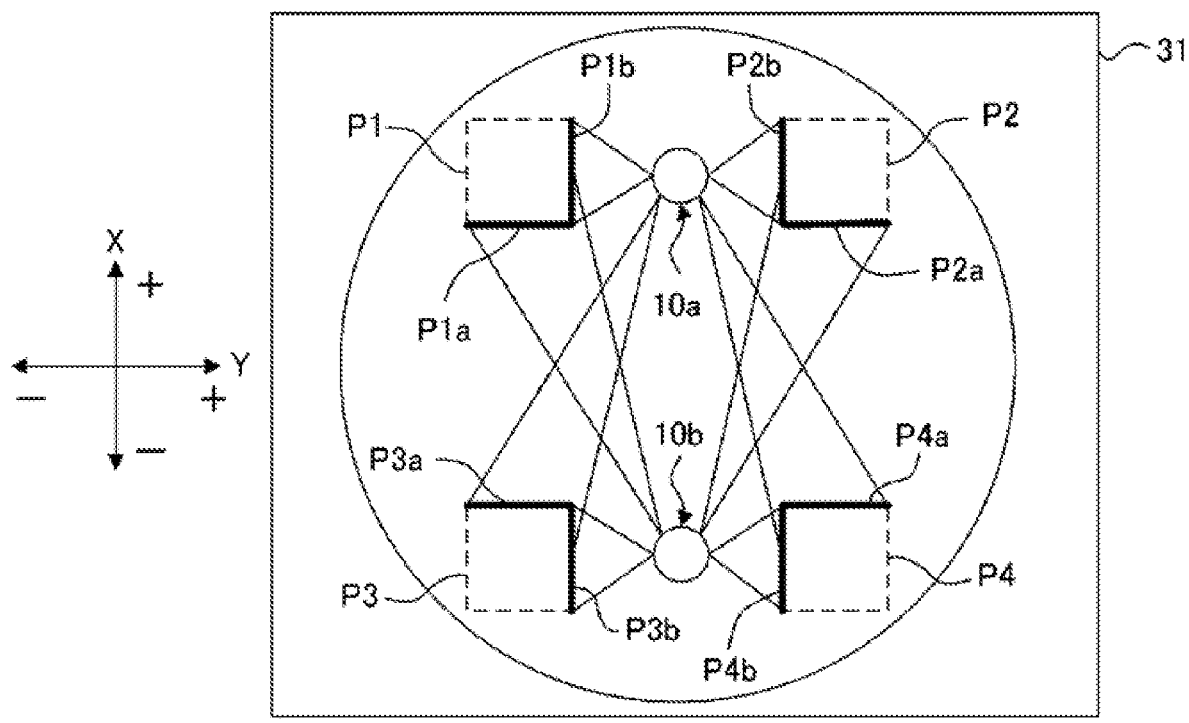
FIG. 7 illustrates a display example of a display unit according to the modification of the present disclosure.

Referring to FIGS. 6 and 7, FIG. 6 is a schematic view of an analysis system according to a modification of the present disclosure, and FIG. 7 illustrates a display example of the display unit according to the modification. The modification of the present disclosure will be described with reference to FIGS. 6 and 7. Like reference numerals refer to like configurations described in the embodiment above, and details thereof are not described herein. For example, since the server 20 and the information terminal 30 according to the present modification have the same configuration as the embodiment above, the server 20 and the information terminal 30 are not illustrated in FIG. 6.

In the modification, as illustrated in FIG. 6, two laser scanners 10a and 10b are used for the four column members P1, P2, P3, and P4 that are identical to the column members of the embodiment above. Specifically, the first laser scanner 10a is placed at a center position between the first column member P1 and the second column member P2, and the second laser scanner 10b is placed at a center position between the third column member P3 and the fourth column member P4.

This layout, as illustrated in FIG. 7, allows the first laser scanner 10a to scan one surface P1b of the first column member P1 and one surface P2b of the second column member P2 in the entire width direction. In addition, the first laser scanner 10a can scan two surfaces P3a and P3b of the third column member P3 and two surfaces P4a and P4b of the fourth column member P4. In the same manner, the second laser scanner 10b can scan one surface P3b of the third column member P3 and one surface P4b of the fourth column member P4, and two surfaces P1a and P1b of the first column member P1 and two surfaces P2a and P2b of the second column member P2.

The two laser scanners 10a and 10b each generate three-dimensional point cloud data and transmit the data to the server, which is not illustrated, and the server integrates the three-dimensional point cloud data. After the integration of the three-dimensional point cloud data, the process proceeds in the same manner as the embodiment above such that the server analyzes the inclination of the column members P1, P2, P3, and P4 and the result of the analysis is displayed on the information terminal.

In the modification above, a plurality of column members P1, P2, P3, and P4 are scanned by a plurality of laser scanners 10a and 10b, and the three-dimensional point cloud data acquired by each of the laser scanners 10a and 10b is integrated. This configuration can reduce blind spots of the column members P1, P2, P3, and P4 in scanning the column members. In particular, if the column members have an uncommon shape or have a complicated layout and the inclination of the entire column members cannot be analyzed with a single laser scanner, it is advantageous to use a plurality of laser scanners. Using a plurality of laser scanners can achieve a stable and efficient plumbing in various construction sites.

Although, in the embodiment above, the column members are rectangular columns, the shape of the column members is not limited to this. For example, if the column members have an H-, T-, or I-shaped cross section, the inclination of the entire column members can be analyzed by detecting at least two mutually perpendicular surfaces of each column member. If the column members are circular columns, the inclination of the entire column members can be analyzed by defining two mutually perpendicular normal vectors to the side surface. The column members may have a hollow cylindrical shape.

Although, in the embodiment above, the display unit 31 displays the degree of inclination by inclination vectors that extend from the surfaces of the column members, the inclination information may be displayed by any other means. For example, the degree of inclination may be displayed by numerical values such as angles. In some embodiments, an allowable limit for the inclination is set in advance, and the display unit 31 may display an inclination vector exceeding the allowable limit in a different color.

Although the analysis system 1 according to the embodiment above is a cloud computing system configured by three devices that are the laser scanner 10, the server 20, and the information terminal 30, the configuration of the analysis system 1 is not limited to this. For example, the functional units (data acquisition unit, surface detector, inclination analyzer, measurement controller) of the server may be included in the information terminal or the laser scanner and the analysis system 1 may be configured only by the information terminal and the laser scanner.

What is claimed is:

1. An analysis system for analyzing inclination of a structure, the analysis system comprising:
   a measuring device configured to receive and emit a measurement light beam from and to the structure horizontally all around the measuring device and in a certain range in a vertical direction, the measuring device configured to scan the measurement light beam and generate three-dimensional point cloud data of the structure;
   a data acquisition unit configured to acquire the three-dimensional point cloud data of the structure;
   a surface detector configured to detect a surface of the structure based on the three-dimensional point cloud data; and
   an inclination analyzer configured to analyze inclination of the structure by calculating inclination of the surface detected by the surface detector.

2. The analysis system of claim 1, further comprising:
   a measurement controller configured to control a measurement range of the measuring device.

3. The analysis system of claim 2, wherein the measurement controller acquires positional information including an installation position of the structure and limits the measurement range of the measuring device to a certain range including the structure based on the positional information.

4. The analysis system of claim 3, wherein the measurement controller acquires the positional information including the installation position of the structure by causing the measuring device to perform a simplified scan for acquiring the installation position of the structure.

5. The analysis system of claim 1, further comprising:
   a display unit configured to display information relating to the inclination of the structure analyzed by the inclination analyzer.

6. The analysis system of claim 5, wherein the display unit represents the information relating to the inclination of the structure by a vector generated from the three-dimensional point cloud data and extending from the surface of the structure.

7. An analysis method for analyzing inclination of a structure, the analysis method comprising:
   receiving and emitting a measurement light beam from and to the structure horizontally all around a measuring device and in a certain range in a vertical direction to scan the measurement light beam, thereby acquiring three-dimensional point cloud data of the structure;
   detecting a surface of the structure based on the three-dimensional point cloud data; and
   analyzing inclination of the structure by calculating inclination of the surface detected at the detecting.

8. A non-transitory storage medium in which an analysis program for analyzing inclination of a structure is stored, the analysis program causing a computer to execute:
   receiving and emitting a measurement light beam from and to the structure horizontally all around a measuring device and in a certain range in a vertical direction to scan the measurement light beam, thereby acquiring three-dimensional point cloud data of the structure;
   detecting a surface of the structure based on the three-dimensional point cloud data; and
   analyzing inclination of the structure by calculating inclination of the surface detected at the detecting.

9. The analysis system of claim 1, wherein the measuring device comprises a horizontally rotatable and vertically swingable structure.

* * * * *